(12) United States Patent
Rosenschein et al.

(10) Patent No.: US 8,684,917 B2
(45) Date of Patent: *Apr. 1, 2014

(54) EMBOLISM FILTER WITH SELF-DEPLOYABLE GUIDEWIRE STOP

(75) Inventors: Uri Rosenschein, D.N. Modiim (IL); Gil Ofir, Even Yehuda (IL)

(73) Assignee: Gardia Medical Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/354,989

(22) Filed: Jan. 16, 2009

(65) Prior Publication Data

US 2009/0149806 A1    Jun. 11, 2009

Related U.S. Application Data

(63) Continuation of application No. 10/523,967, filed as application No. PCT/IL03/00144 on Feb. 25, 2003, now Pat. No. 7,479,151.

(60) Provisional application No. 60/400,801, filed on Aug. 5, 2002.

(51) Int. Cl.
*A61M 29/00*    (2006.01)

(52) U.S. Cl.
USPC .......................................... 600/200

(58) Field of Classification Search
USPC ................. 606/108, 194, 200, 192; 600/585; 623/1.11, 1.12
See application file for complete search history.

(56) References Cited

U.S. PATENT DOCUMENTS

| | | | | |
|---|---|---|---|---|
| 4,395,806 | A * | 8/1983 | Wonder et al. | 29/890.122 |
| 5,273,052 | A * | 12/1993 | Kraus et al. | 600/585 |
| 5,312,341 | A * | 5/1994 | Turi | 604/103.05 |
| 5,785,715 | A * | 7/1998 | Schatz | 606/108 |
| 5,919,162 | A * | 7/1999 | Burns | 604/99.01 |
| 6,270,465 | B1 * | 8/2001 | Keith et al. | 600/585 |
| 6,537,295 | B2 * | 3/2003 | Petersen | 606/200 |
| 7,479,151 | B2 * | 1/2009 | Rosenschein et al. | 606/200 |
| 8,152,832 | B2 * | 4/2012 | Beulke et al. | 606/200 |
| 8,262,690 | B2 * | 9/2012 | Petersen | 606/200 |
| 2002/0032486 | A1 * | 3/2002 | Lazarovitz et al. | 623/23.67 |
| 2003/0083692 | A1 * | 5/2003 | Vrba et al. | 606/200 |
| 2003/0199861 | A1 * | 10/2003 | Lafontaine | 606/21 |
| 2003/0212434 | A1 * | 11/2003 | Thielen | 606/200 |
| 2007/0088384 | A1 * | 4/2007 | Vrba et al. | 606/200 |

* cited by examiner

*Primary Examiner* — Darwin Erezo
*Assistant Examiner* — Amy Shipley
(74) *Attorney, Agent, or Firm* — Novak Druce Connolly Bove + Quigg LLP

(57) ABSTRACT

An embolism filter adapted to selectively stop an embolism filter along a length of guidewire, including a filter adapted to encircle a guidewire and at least one self-deploying stop attached to the filter and which selectively stops movement of said filter.

14 Claims, 8 Drawing Sheets

EMBOLISM FILTER WITH SELF-DEPLOYABLE GUIDEWIRE STOP

RELATED APPLICATIONS

The present application is a continuation of U.S. patent application Ser. No. 10/523,967, filed Dec. 6, 2005, now U.S. Pat. No. 7,479,151, which is a U.S. National Phase of PCT Application No. PCT/IL2003/000144, filed on Feb. 25, 2003, published as WO 2004/012628, which claims the benefit under 35 USC §119(e) of U.S. provisional application 60/400,801, filed on Aug. 5, 2002, the disclosure of which is incorporated herein by reference.

FIELD OF THE INVENTION

The present invention relates to devices for filtering embolitic material from circulating blood.

BACKGROUND OF THE INVENTION

Embolitic material comprising calcium, intimal debris, pieces of an artheromatous plaque and/or thrombi, has the potential of migrating and causing distal tissue damage, for example, stroke and/or myocardial infarction. (See Topol, E. J. and Yadov, J. S., "recognition of the Importance of Embolization in Athereosclerotic Vascular Disease", *Circulation* 2000, 101:570.) Embolic material with the potential of distal tissue damage is often released during vascular interventional procedures, for example, stenting of an artheromatous region.

In response to the risk posed by released emboli during vascular intervention procedures, a mesh filter mounted on a specially adapted guidewire may be introduced into a blood vessel to strain released embolitic material from the circulation, thereby reducing the risk of distal tissue damage. To deploy such a mesh filter, a specially designed guidewire, for example having a built-in stop, may be placed in the blood vessel so that the stop is just distal to the target area. A collapsed filter is advanced along the guidewire until it is prevented from further advancement by the stop and opened so that it catches debris released from the target area.

Unfortunately, the specially designed guidewire is bulky and hard to manipulate due, in part, to the incorporated stop and accurate positioning of the filter is difficult once it has reached the guidewire stop. In addition, the use of a non-standard guidewire may require replacement or stocking of new catheterization sets.

Tsugita et al. in U.S. Pat. No. 6,361,971 B1 and US Applications 2002/0095174 and 2002/0183782, the disclosure of which is incorporated hereby in its entirety by reference, demonstrate filters and locking mechanisms.

SUMMARY OF THE INVENTION

An aspect of some embodiments of the invention relates to an embolism filter stop and method for its deployment, comprising a filter with one or more self-deploying stops attached thereto that stop the filter at substantially any desired location along a length of guidewire.

According to an exemplary embodiment of the present invention, the filter with its self-deploying stops can be deployed on guide wires in a variety of lengths and/or a variety of diameters. Alternatively or additionally, different stop designs and/or materials may be used for specific guidewires with specific properties, for example a flexible and/or small gage wire that may be used in fetal surgery. It is a particular feature of some embodiments of the invention, that the filter can be deployed on a substantially smooth guide wire, with no projections (where the filter is deployed) and/or with a uniform diameter in such a section. However, the filter can also be deployed with non-standard guide wires, for example, with a stepped or tapered diameter or with stops, ignoring or utilizing these stops, depending on the filter geometry.

In an exemplary embodiment, the at least one stop comprises is self-expanding, for example comprising a spring. Alternatively or additionally, the at least one self-expanding stop comprises a cushion made of, for example, a flexible rubber material. Additionally or alternatively, the at least one self-expanding stop comprises a fluid-filled flexible compartment containing compressed fluid, for example a gas that expands upon removal of a restrainer.

In an exemplary embodiment, a restrainer prevents the one or more stops from prematurely contacting and locking to the guidewire. Upon reaching the target tissue, the restrainer is pulled free and the stop self-deploys, fixing the filter in place. Optionally, the at least one stop comprises at least two stops that are, for example, symmetrically disposed around said wire and/or apply symmetric and/or equivalent force around the wire. Alternatively or additionally, the stops provide equal amounts of motion (e.g., while expanding) on opposing sides of the guide wire and/or on axially spaced locations on the guidewire, so that the placement of the filter is parallel to the guide wire. in some embodiments, an intentionally skewed placement of the filter may be desirable.

In an alternative embodiment of the invention, the stop is not self-deploying but is integral to and mechanically coupled to the filter and is activated other than by the guidewire. In one example, the stop is a deforming and/or expandable element, such as an inflatable balloon having an inflation port to which an inflation hose is attached. In an exemplary embodiment, the port self-seals following inflation of the balloon and removal of the hose. If the balloon is elastic, it can also be restrained after inflation.

Optionally, the filter defines a front and rear boundary and the at least one stop is connected to at least one of said boundaries. In an exemplary embodiment, the at least one stop is substantially contained between said boundaries, for example, so the overall length of the filter is conserved, allowing the filter to be easily maneuvered in the vasculature. Alternatively or additionally, said at least one stop projects beyond one or more of said boundaries.

An aspect of some embodiments of the invention relates to a filter that has some axial freedom of motion relative to a guidewire, after it is locked in place on a guidewire. In an exemplary embodiment of the invention, the filter deploys around a sleeve that travels along a guidewire, said, sleeve having one or more stops shiftably attached thereto. In an exemplary embodiment, the shiftable stops allow the open filter to remain stationary in relation to the vascular environment even if the guidewire is moved a small amount. In this manner, a shiftable stop limits movement of the open filter that may cause trauma to the surrounding tissue, during for example, positional adjustments of a guidewire.

In an exemplary embodiment, the filter comprises one or more support members, for example struts that support the filter membrane and/or slide along the sleeve during deployment and/or collapse of the filter.

In an exemplary embodiment, a sleeve capable of traveling along a guidewire, comprising one or more self-deploying stops, is used in conjunction with one or more devices deployed in the vasculature or in other hollow organs of the body, for example an arthroscopic fiber optic cable, brachytherapy device and/or a laser, using these devices as its guidewire.

There is thus provided in accordance with an exemplary embodiment of the invention, an embolism filter adapted to selectively stop an embolism filter along a length of guidewire, said filter comprising:

a) a filter adapted to encircle a guidewire; and b) at least one self-deploying stop attached to said filter and adapted to selectively stop movement of said filter. Optionally, said at least one stop comprises a spring. Optionally, said spring expands during deployment.

Alternatively or additionally, at least a portion of said stop is removably attached to said filter.

In an exemplary embodiment of the invention, said at least one stop comprises a cushion. Alternatively or additionally, said at least one stop comprises a chamber containing an expandable fluid. Optionally, said filter comprises a fluid release mechanism adapted to cause the release of said expandable fluid.

In an exemplary embodiment of the invention, said at least one stop is adapted to be restrained from contacting said guidewire by at least one stop restrainer. Optionally, said at least one stop is adapted to self-deploy upon removal of said restrainer. Alternatively or additionally, said restrainer comprises a material that changes configuration in response to contact with blood tissue.

In an exemplary embodiment of the invention, said at least one stop comprises at least one inflatable member.

In an exemplary embodiment of the invention, said at least one stop comprises at least two stops. Optionally, said at least two stops are radially disposed around said wire. Alternatively or additionally, said at least two stops are adapted to apply substantially equivalent force to said wire.

In an exemplary embodiment of the invention, said filter is adapted to collapse within a restrictive cavity. Alternatively or additionally, said filter is adapted to self-expand upon exiting a restrictive cavity. Alternatively or additionally, said restrictive cavity comprises a delivery sheath. Optionally, said delivery sheath is removably coupled to said filter.

In an exemplary embodiment of the invention, at least one of said one or more stops are adapted to move a limited distance along said filter.

In an exemplary embodiment of the invention, said filter comprises a sleeve surrounding said one or more stops. Optionally, said stops do not extend beyond at least one end of said sleeve. Alternatively or additionally, said filter is mounted on said sleeve and does not extend axially beyond said sleeve.

There is also provided in accordance with an exemplary embodiment of the invention, a method for stopping motion of a filter along a guidewire comprising:

a) positioning a guidewire in a blood vessel;

b) advancing along said guidewire a filter having at least one stop attached thereto; and c) allowing said stop to self-deploy and engage said guidewire, thereby securing said filter along said guidewire. Optionally, the method comprises expanding said filter. Alternatively or additionally, the method comprises, collecting particulate matter in the filter. Optionally, the method comprises collapsing said filter with said collected particulate matter. Optionally, the method comprises removing said filter with said collected particulate matter from said blood vessel. Optionally, removing said filter comprises not removing said guidewire.

There is also provided in accordance with an exemplary embodiment of the invention, a guidewire stop, comprising:

a) a sleeve that slideably engages a guidewire; and b) at least one self-deploying stop attached to said sleeve that selectively stops movement of said sleeve along said guidewire. Optionally, the stop includes a vascular filter having front and rear boundaries wherein said sleeve is attached to at least one of said boundaries. Optionally, said sleeve is extends beyond at least one of said boundaries. Alternatively, said sleeve is substantially contained between said boundaries.

There is also provide din accordance with an exemplary embodiment of the invention, an embolism filter adapted to selectively stop an embolism filter along a length of guidewire, said filter comprising:

a) a filter adapted to encircle a guidewire; and b) at least one deformable stop attached to said filter and adapted to selectively stop movement of said filter. Optionally, said stop comprises an inflatable stop. Optionally, the filter comprises a removal sheath adapted to puncture said stop.

BRIEF DESCRIPTION OF THE DRAWINGS

Exemplary non-limiting embodiments of the invention are described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EXEMPLARY EMBODIMENTS

Filter with Spring Stops

Figure 1:
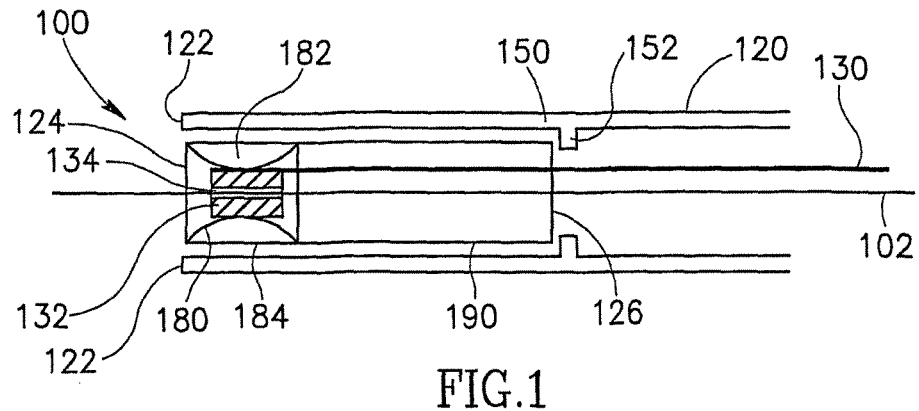
FIGS. 1-3 are cross sectional schematic views showing the operation of an embolism filter and its self-deploying stops, in accordance with an exemplary embodiment of the invention.

FIG. 1 is a cross sectional view of a filter 100 contained within a delivery sheath 150, in accordance with an exemplary embodiment of the invention. In an exemplary embodiment, filter 100 comprises stops 180 and 182 that are restrained from contacting a guidewire 102 by a restrainer 132. During positioning of filter 100, optional stabilizers 152 that project from a sheath wall 120 press against filter 100 to advance filter 100 along guidewire 102.

Filter 100 and/or stops 180 and 182 may be designed in a variety of materials and shapes for example a range of guidewire diameters, for example a range of 1:1.5, 1:2 or 1:4 or any smaller, intermediate or larger ratio of diameters. Alternatively or additionally, in any specific design, filter 100 and/or stops 180 and 182 may be manufactured to encompass a guidewire of a specific diameter. Guidewire diameters for which filter 100 and/or stops 180 and 182 can be designed include, for example:

i) small gage flexible guidewires for use in peripheral vasculature, for example having a diameter of 0.014, 0.018, 0.032 or 0.035 inches;

ii) guidewires designed for coronary surgery, for example having a diameter of 0.014.

iii) specially designed guidewires designed for coronary interventions and/or fetal surgery, having diameters smaller than 0.014, greater than 0.035 and/or having non-standard diameters between 0.014 and 0.035 inches.

In an exemplary embodiment, restrainer 132 has a passage 134 that rides along wire 102 and permits movement of filter 100 distal to the target tissue location.

In an exemplary embodiment, a front boundary 122 of delivery sheath may be tapered to facilitate easy movement through the vasculature. Additionally or alternatively, front boundary 122 may be curved in towards wire 102. Optionally, front boundary 122 comprises a flexible material so that it allows filter 100 to exit in spite of being unvaccinated.

In an exemplary embodiment, front boundary 124 of a sleeve wall 184 is tapered to ease advancement of filter 100 through the vasculature. Additionally or alternatively, a rear boundary 126 is tapered to facilitate retreat of filter 100 through the vasculature.

Optionally, stops 180 and/or 182 are contained internal to wall 184, for example near or at front boundary 124 and/or rear boundary 126 of filter 100, so the overall length of filter 100 is conserved. Having a shorter profile associated with internally contained stops 180 and/or 182, may assist filter 100 in maneuvering in the vasculature. Alternatively or additionally, stops 180 and/or 182, within wall 184, project beyond front boundary 124 and/or rear boundary 126 of filter 100. In an exemplary embodiment, stops 180 and/or 182 comprises springs, for example a spring steel, or resilient plastic.

Deployment of stops 180 and 182 may be actuated, for example, by using restrainer 132 that is remotely controlled, for example using an RF signal to cause its displacement and/or dissolution. Alternatively, other methods of actuation of stops 180 and 182 are contemplated, for example, restrainer 132 may dissolve or fall apart in the presence of blood or under the action of RF radiation or ultrasonic radiation.

Figure 2:
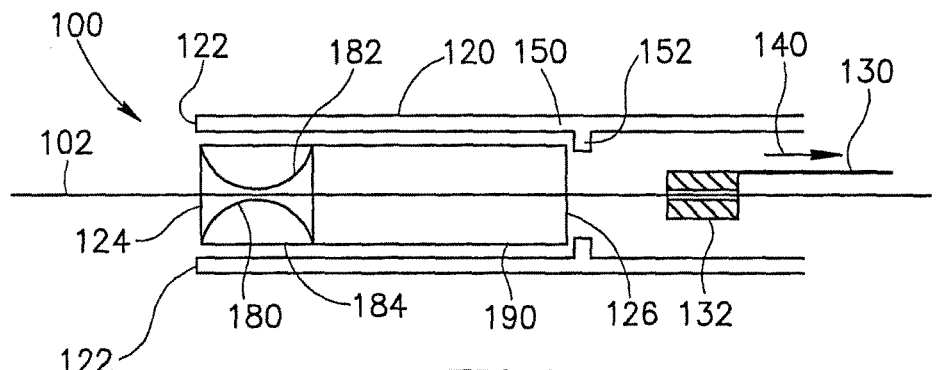

In FIG. 2, delivery sheath 150 remains around filter 100 and stabilizers 152 press against filter 100 while restrainer 132 is pulled away from stops 180 and 182, using a restrainer cable 130 to pull restrainer 132 in a direction 140. In an exemplary embodiment, restrainer 132 has a length of between 1-4 centimeters. Optionally restrainer 132 is less than 1 or 0.5 centimeter in length when used, for example, with small stops 180 and/or 182, designed for fetal and/or pediatric procedures. Optionally restrainer 132 has a length of greater than 4 centimeters when used, for example, with stops 180 and/or 182, for example, that are 3 or 4 centimeters or more in length for use when filter 100 is larger, for example where large amounts of particulate matter is anticipated that cannot be contained by a smaller filter. Restrainer 132 is optionally flexible in bending, even if it is not compressible, for example it may be segmented into narrow rings that are interconnected by a soft material.

Optionally, restrainer 132 is removed from contact with stops 180 and/or 182 by pulling restrainer cable 130 so that restrainer 132 shifts approximately 1 centimeter with respect to stops 180 and/or 182. In pediatric and/or large vessel use, when smaller or larger stops 180 and/or 182 are used, restrainer 132 may require less than 1 centimeter or greater than 1 centimeter of movement to allow stops 180 and/or 182 to expand.

Figure 3:
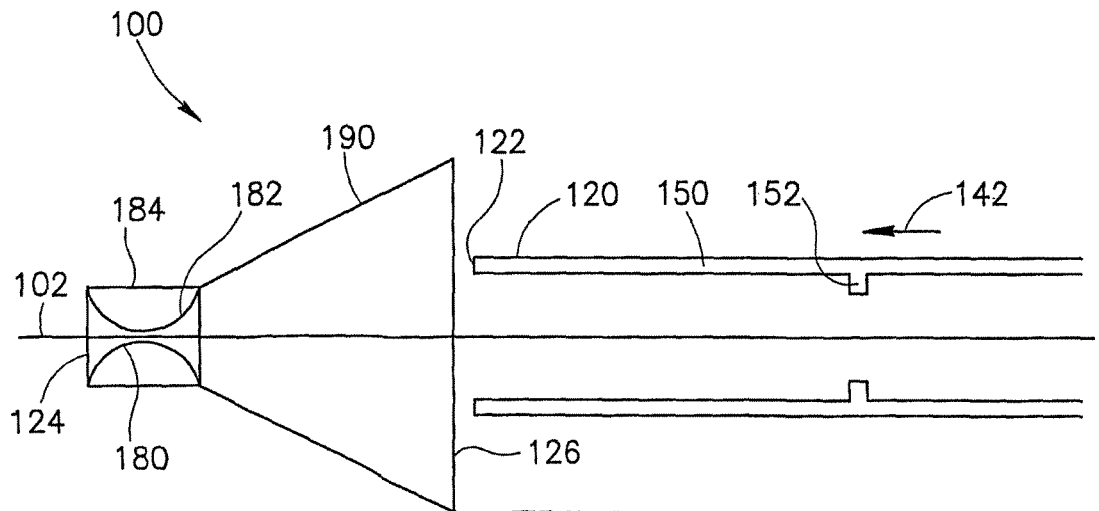

With restrainer 132 removed, stops 180 and 182 expand to contact guidewire 102 thereby fixing filter 100 in place along guidewire 102. With filter 100 fixed in place, stops 180 and 182 stabilize filter 100 so that sheath 150 can be pulled away from filter 100 as seen, for example, in FIG. 3.

With delivery sheath 150 removed from filter 100, a porous filter membrane 190 expands, for example as a result of blood flow pressure against it, to act as a filter, serving to strain particulate matter from the blood. Alternatively or additionally, filter 100 is made of resilient material that self-expands as it is freed of delivery sheath 150.

Optionally, delivery sheath 150 is moved in a direction 142 against filter membrane 190, thereby causing filter membrane 190 to collapse. With membrane 190 collapsed, filter 100, guide wire 102 and sheath 150 are removed from the blood vessel. Using a guidewire of uniform diameter and/or without projections to aid in positioning filter 100, is potentially advantageous as any number of additional devices, for example stents, can be interchangeably used with any guidewire 102 and any filter 100. Stents of a variety of diameters, for example, can be stocked separately of guidewires 102 and/or filters 100 of different diameters. This reduces inventory costs associated with packaging each diameter of stent in multiple packages, each package containing a different diameter and/or design of guidewire 102 and/or filter 100.

Sleeve with Inflatable Stops

Figure 4:
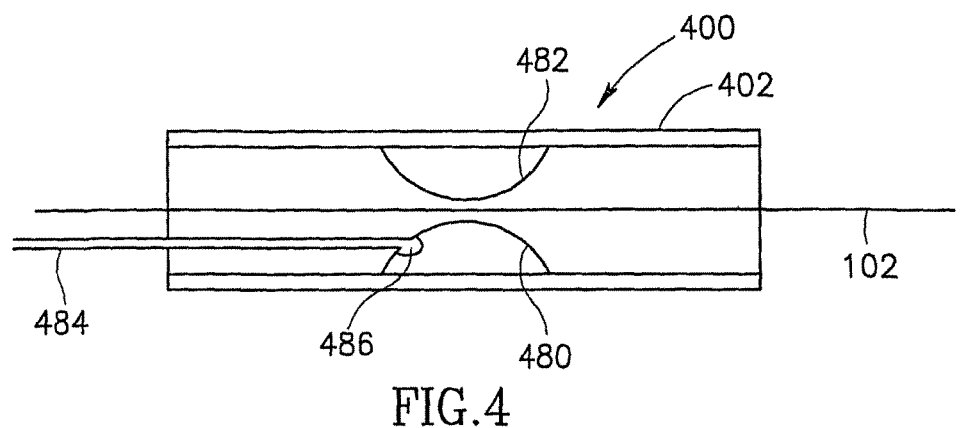
FIGS. 4-6 are cross sectional schematic views of various embodiments of guidewire sleeves with stops, in accordance with an exemplary embodiment of the invention.

In an alternative stop mechanism to spring stops 180 and 182, FIG. 4 shows a cross sectional view of a sleeve stop 400 having an outer wall 402 from which one or more inflatable balloon stops 480 and 482 project. In an exemplary embodiment, sleeve is delivered to a target site and an inflation hose 484 connected to one or more inflatable balloon stops 480 and/or 482 is used to transfer fluid into balloons 480 and/or 482 thereby causing their expansion. Balloons 480 and/or 482 expand until they contact wire 102, thereby preventing further movement of sleeve stop 400. In an exemplary embodiment, a hose attachment port 486, self-seals following inflation of balloons 480 and/or 482 and removal of hose 484.

In an exemplary embodiment fluid contained in balloons 480 and 482 is biologically inert so that its introduction into the blood stream will not cause any untoward sequella. In an exemplary embodiment, sleeve stop 400 may be removed from the blood vessel without removing guide wire 102, for example using the following technique:

1. A sheath having one or more sharp projections at its leading edge, for example, is fed along guidewire 102 until its leading edge contacts balloons 480 and/or 482.

2. The sheath is pressed against sleeve stop 400 so that the one or more sharp projections puncture balloon 480 and/or 482, allowing the biologically inert fluid within to escape harmlessly into the blood stream.

3. A retrieval sheath is introduced along guide wire 102 and sleeve stop 400 is pulled into the retrieval sheath, using methods well known in the art, for example. Optionally, the retrieval sheath includes one or more retractable hooks that engage and pull back the filter portion, so that it collapses. Alternatively or additionally, the retrieval sheath includes a cooling material, which when applied to a filter made of a suitable shape memory material causes the filter to change its shape to a collapsed filter. The retrieval sheath containing sleeve stop 400 is removed from the blood vessel while guidewire 102 is optionally left in place. The retrieval sheath may be provided before balloons 480 and 482 are deflated.

Alternatively or additionally, inflation hose 484 is coupled to balloons 480 and/or 482 so that removal of hose 484 leaves an opening in balloons 480 and/or 482. Hose 484 is left in place following expansion of balloons 480 and/or 482 until, for example, sleeve stop 400 requires removal.

To remove sleeve stop 400 without removing guidewire 102, the following procedure is optionally followed:

1. Inflation hose 484 is pulled so that it disconnects from inflatable balloon stops 480 and/or 482. Disconnection of hose 484 allows the biologically inert fluid to escape harmlessly into the blood stream and balloons 480 and/or 482 deflate.

2. Sleeve stop 400 is pulled into a retrieval sheath and removed as noted above in previous step 3.

Sleeve with Expanding Cushion Stops

Figure 5:
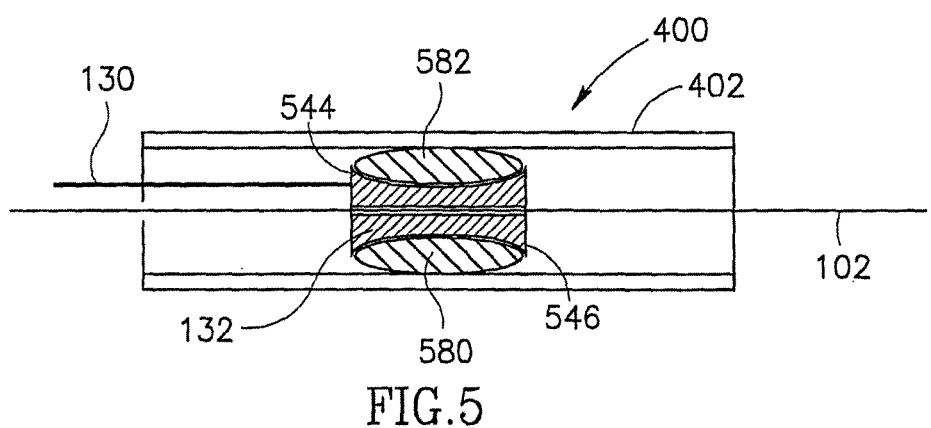

In another alternative stop mechanism to spring stops 180 and 182, FIG. 5 shows a cross sectional view of a sleeve stop 400. Sleeve stop 400 has outer wall 402 from which one or more self-expanding cushions, 580 and/or 582 are restrained from contacting wire 102 by restrainer 132. In an exemplary embodiment, after sleeve stop 400 reaches its target area, restrainer 132 is pulled away from sleeve 400 using restrainer cable 130, thereby allowing cushions 580 and/or 582 to deploy and fix sleeve 400 in place. These cushions may be formed, for example, out of silicone polymers.

Alternatively or additionally, cushions 580 and/or 582 comprise expanding absorbent materials that, for example, absorb intravascular fluid and expand. Restrainer 132, for example, compresses cushions 580 and/or 582 so they are prevented from absorbing fluid until they are freed from restrainer 132.

With cushions 580 and/or 582 comprising fluid-absorbing embodiments, restrainer 132, for example, may comprise a layer of materials 544 and/or 546 that interfaces with cushions 580 and/or 582 to prevent fluid from being absorbed. Upon displacement of materials 544 and/or 546, for example with removal of restrainer 132, fluid absorption by cushions 580, and/or 582 subsequently takes place.

Compressed Gas Stops

Figure 6:
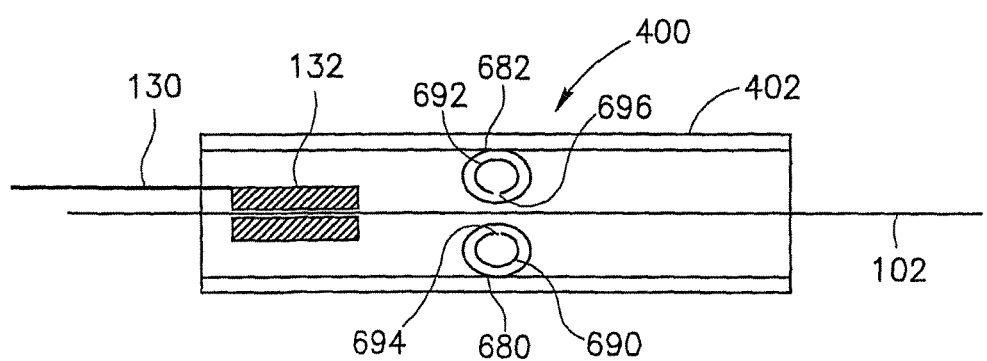

FIG. 6 is an alternative embodiment of self-deploying sleeve stop 400 having outer wall 402 from which project one or more flexible compartments 680 and/or 682 containing compressed gas. In an exemplary embodiment, restrainer 132 is removed from flexible compartments 680 and/or 682, so that the compressed gas within expands, causing flexible compartments 680 and/or 682 to expand and contact guidewire 102.

Optionally, compartments 680 and/or 682 contain compressed gas canisters 690 and 692 respectively that are restrained from expanding by restrainer 132. Upon removal of restrainer 132, for example, the compressed gas breaks through a weak spot 694 in canister 690 and/or a weak spot 696 in canister 692, allowing compressed gas to escape and expand compartments 680 and/or 682.

Alternatively or additionally, 694 and 696 comprise openings in canisters 690 and 692 respectively. In an exemplary embodiment, restrainer 132 press the walls of compartments 680 and/or 682 compress against openings 694 and 696 so they remain sealed. Upon removal of restrainer 132, walls of compartments 680 and/or 682 remove from openings 694 and 696, allowing gas to expand into compartments 680 and/or 682.

Membranous Filter with Guide Stop Sleeve

Figure 7:
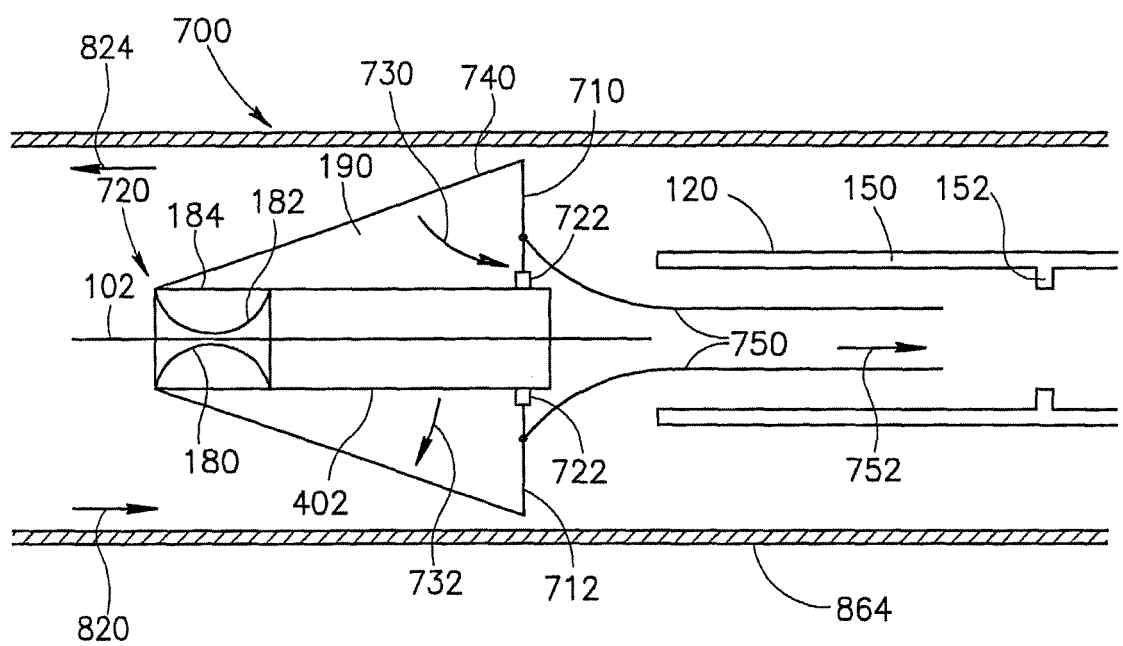
FIG. 7 is a schematic view of a sleeve and guidewire stop in combination with a filter, in accordance with an exemplary embodiment of the invention.

FIG. 7 is a sleeved guidewire stop and filter 700, in accordance with an exemplary embodiment of the invention, comprising outer wall 402 with stops 180 and 182, in accordance with an exemplary embodiment of the invention.

In an exemplary embodiment, porous membrane filter 190 has one or more living (or other type) hinge attachments 720 to outer wall 402, allowing filter 190 to pivot open or closed in relation to wall 402, during expansion and/or collapse. The hinge attachment of porous filter 190 to wall 402 may comprise a variety of materials, for example, different formulations of resilient plastics. Alternatively or additionally, attachment of porous filter 190 to wall 402 may comprise alternative designs, for example, one or more hooks passing through one or more eyes.

In an exemplary embodiment, porous membrane 190 has one or more struts 710 and/or 712 attached to a circumferential ring 722. Struts 710 and/or 712 support porous membrane 190 and circumferential ring 722 slides along outer wall 402 during deployment and/or collapse of struts 710 and/or 712. For example, as a filter surface 740 moves in a direction 732, strut 710 and/or circumferential ring 722 move in a direction 730, so that filter 700 assumes the deployed configuration shown.

In an exemplary embodiment, movement of strut 710 in direction 730 and/or movement of filter surface 740 in direction 732 is automatic when they exit from sheath 150. Alternatively or additionally, an operator-controlled mechanism, for example a membrane filter deployer cable 750 is pulled in a direction 752 so that struts 710 and/or 712 move radially outward from guidewire 102 until membrane 190 is in the deployed position.

In an exemplary embodiment, following expansion, filter 190 serves to trap particulate matter, for example, one or more of pieces of an artheromatous plaque, thrombi, and/or gas. Following completion of the procedure, filter 190 is collapsed and removed along with the particulate matter, for example, with guide wire 102.

In an exemplary embodiment, porous membrane 190 and/or struts 710 and/or 712 contact the inner surface of blood vessel 864 to form a seal and/or substantially span blood vessel 864 so that at least a substantial amount, if not all, blood passing through blood vessel 864, is filtered by membrane 190.

Blood vessel size may be from 2-8 millimeters in diameter, and even less than 2 millimeters or greater than 8 millimeters in certain areas and/or individuals. Optionally, to accommodate this range in blood vessels, different embodiments of porous membrane 190 and/or struts 710 and/or 712 may exhibit different degrees of radial expansion or may be partially deployed.

For example, in vessels 864 with a smaller diameter, struts 710 and/or 712 may deploy so they are not maximally expanded with respect to guidewire 102, while in larger blood vessels, struts 710 and/or 712, for example, may approach their maximal expansion configuration.

Filter with Shiftable Stops

Figure 8A:
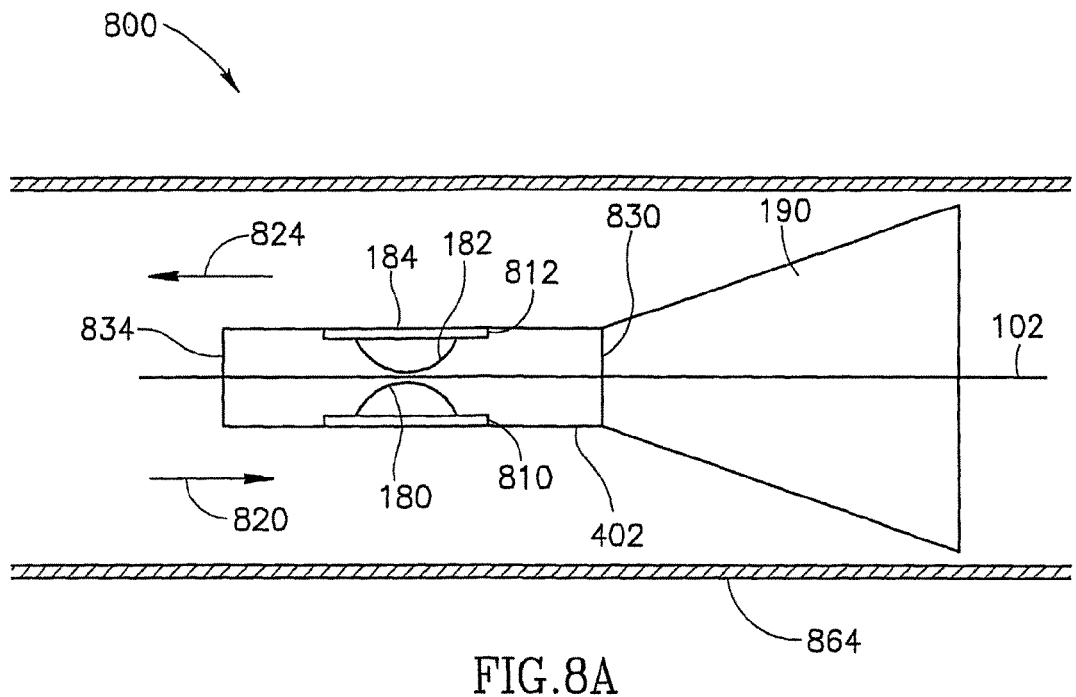
FIGS. 8A and 8B are schematic views of a shiftable filter stop, in accordance with an exemplary embodiment of the invention.

FIG. 8A is a filter 800 with shiftable guidewire stop 180, mounted on a shift platform 810 and guidewire stop 182, mounted on a shift platform 812. Shiftable stops 180 and/or 182 shiftably secure sleeve wall 184 in relation to guidewire 102. In this and other embodiments it should be noted that platforms 810 and 812 may be a single tubular platform and that stops 180 and 182 maybe a single tubular stop. Use of separate elements, however, especially in this embodiment, may allow some extra freedom in accommodation of shifting and/or other movement (e.g., bending) of guide wire 102.

Figure 8B:
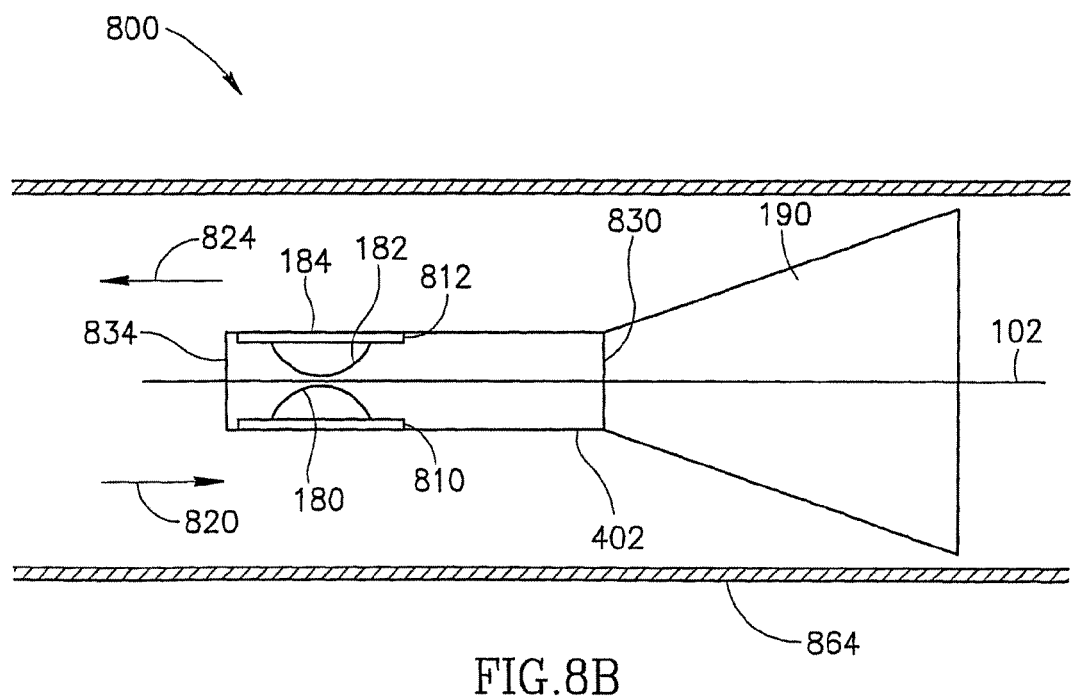

FIG. 8B shows filter 800 remaining stationary relative to blood vessel 864, while platform 812 and guidewire 102 move a small amount in a direction 824.

The degree of allowed shifting may depend, for example, on an inner geometry of wall 184, for example, if rails are provided for the platforms and/or if stops are provided for the platforms, for example at the ends of wall 184.

In an exemplary embodiment, shift platform 810 shifts in relation to sleeve wall 184, for example one centimeter in direction 824, or one centimeter in direction 820. Greater or smaller amounts of shifting may be allowed, for example, between 2 and 5 mm, or greater or smaller amounts. Filter 800 is optionally designed to shift in a symmetrical manner, once deployed.

Alternatively or additionally, filter 800 may be used in an environment where shifting in direction 820 is anticipated to be different than shifting in direction 824. For example where multiple stents are being placed one after the other, filter 800 may need to shift more in direction 820 than in direction 824. Alternatively or additionally to axial shifting, rotational shifting may be allowed, for example by providing rotational freedom (optionally with one or more stops) between platform 810 and sleeve 184.

In an exemplary embodiment, shiftable stops 180 and/or 182 are confined in their movement, for example, within a rear sleeve boundary 830 and/or a front sleeve boundary 834. Changing the distance between boundaries 830 and 834, increases or decreases the excursion available to stops 180 and 182 in relation to wall 184.

Optionally filter 800 may be designed so that sleeve wall 184 has a greater excursion than plus or minus one centimeter in relation to platforms 810 and 812, for example in large diameter blood vessels. Alternatively or additionally filter 800 may be designed so that sleeve wall 184 has a smaller excursion in relation to platforms 810 and 812, for example in small diameter blood vessels in fetal applications. In an exemplary embodiment, platforms 810 and 812, for example, comprise a ring that is shiftably mounted against sleeve wall 184.

Alternatively or additionally to free shifting, platforms 810 and 812 are elastically attached to sleeve wall 184, for example to absorb shock caused by sudden movement of guidewire 102 (and then optionally realign the filter in accordance with the new guidewire position), or to encourage smaller amounts of shifting.

Referring back to FIG. 7, to show a potential advantage of using a shiftable filter, upon deployment of shiftable filter 700, filter membrane 190, for example, contacts a blood vessel wall 864, for example, around its perimeter. Pressure on filter 700 in directions 824 and/or 820, for example due to movement of guidewire 102, may cause movement of filter 700, so that filter membrane 190 scrapes blood vessel wall 864, possibly causing damage to blood vessel. Alternatively, distortion of the filter may occur, which may also be undesirable.

By allowing movement of shiftable filter 800 as sleeve 184 moves in relation to shift platforms 810 and 812, shiftable filter 800 remains stationary with respect to blood vessel wall 864 even when there is movement pressure in directions 820 and/or 824. By limiting movement of shiftable filter 800 with respect to blood vessel wall 864, trauma to wall 864 is possibly reduced and/or eliminated.

Filter Structure Detail

Figure 9:
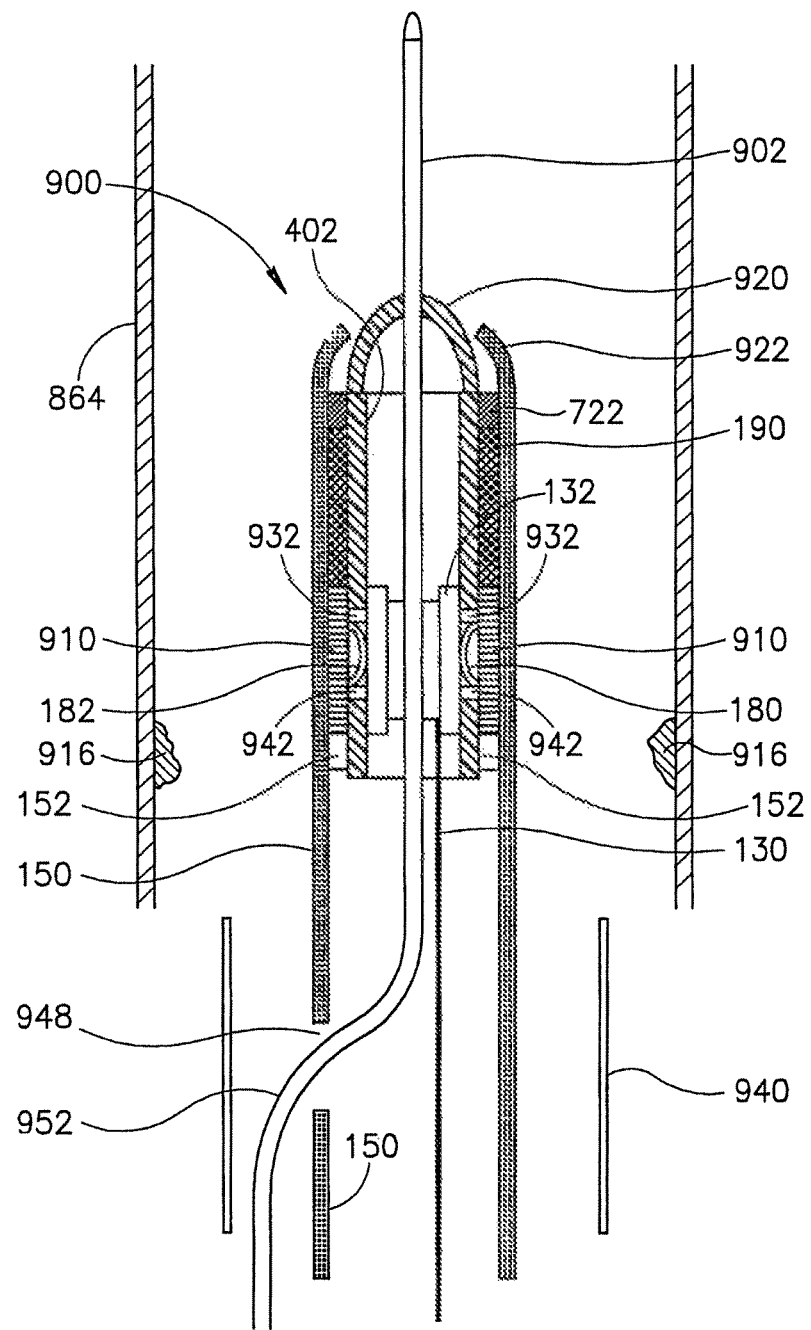
FIG. 9 is a detailed cross sectional view of a filter during delivery in a blood vessel, in accordance with an exemplary embodiment of the invention.

FIG. 9 is a detailed cross sectional view of a filter 900 and stops 180 and 182 during delivery in a blood vessel 864, in accordance with an exemplary embodiment of the invention. In an exemplary embodiment, stops 180 and/or 182 are limited in movement by a forward limiter 932 and a rear limiter 942. Stops 180 and/or 182, for example, are attached to limiters 932 and 942. Limiters 932 and/or 942 may be fixed to wall 402, slideably attached to wall 402 and/or slideably attached to wall 402 for example so that limiters 932 and/or 942 move only under a relatively large displacement force.

In an exemplary embodiment, delivery sheath 150 has an opening 948 that allows filter 900 to be deployed on a guidewire 902 using a rapid exchange and/or a monorail technique. In a monorail technique, guidewire 902 does not require excursion along the length of delivery sheath 150, for example two meters or more.

In an exemplary embodiment, to facilitate rapid deployment, sleeve 150, for example has curved section 922 that curves toward guide wire 902. Curved section 922, for example, may be advantageous in that it aids sheath 150 in passing easily through blood vessel 864 without scraping walls of blood vessel 864.

Alternatively or additionally, curved section 922 edges may be beveled along the front boundary. Beveling the edges of curved section 922 may be advantageous in that it aids in placement of filter 900 without causing trauma to surrounding tissue. Outer wall 402 optionally contains curved tip 920 to additionally aid in placement of filter 900 without causing tissue trauma. Section 922 and/or tip 920 optionally seal against guidewire 902, to prevent blood flow between them.

In an exemplary embodiment, filter 900 has a curved section 920 that allows movement of filter 900 against blood vessel 864 without causing trauma during a rapid exchange technique.

In an exemplary embodiment, struts 910 are collapsed within deployment sheath 150, along with filter 190 that is attached to circumferential ring 722.

Figure 10A:
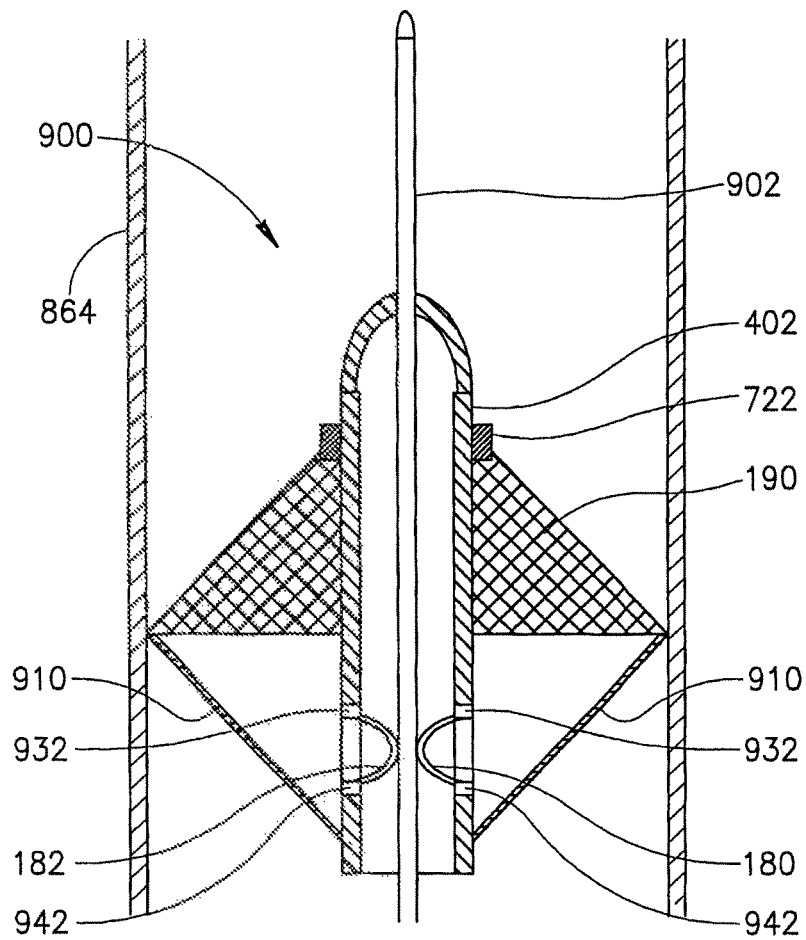
FIG. 10A is a detailed cross sectional view of a filter following deployment in a blood vessel, in accordance with an exemplary embodiment of the invention.

FIG. 10A is a detailed cross sectional view of filter 900 following expansion of stops 180 and 182 and removal of delivery sheath 150. Upon removal of delivery sheath 150, for example, struts 910 and/or filter membrane 190 have expanded radially outward, in accordance with an exemplary embodiment of the invention.

In an exemplary embodiment, rings 932 and 942 are fixed in place along wall 402, while ring stops 180 and 182, for example, deform under pressure from restrainer 132 (FIG. 9). Deformation of stops 180 and 182, for example, may comprise undulations along stops 180 and 182. Upon removal of restrainer 132, stops 180 and 182 expand to a final state shown schematically in FIG. 10A.

Figure 10B:
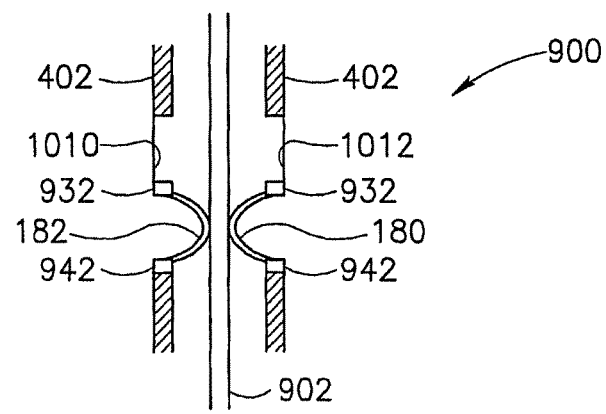
FIG. 10B is a partial detailed cross sectional view of the filter shown in FIG. 10A, in accordance with an exemplary embodiment of the invention.

FIG. 10B is an alternative embodiment of stops 180 and 182 shown in FIG. 10A. Filter 900 comprises ring 942 that is fixed in place along wall 402 and ring 932 that is slideably connected to wall 402. In an exemplary embodiment, upon removal of restrainer 132, spring stops 180 and 182 change their profile. To accommodate this change in profile, ring 932 slides along wall 402, for example leaving gaps 1010 and 1012 respectively.

Porous membrane 190, for example, is made of materials having pores of 200 microns in diameter, though it could have pores of between 20 and 250 microns, depending upon anticipated type and size of debris.

In delicate fetal procedures, for example fetal hydrocephalic shunt placement, pore size may be below 20 microns, while in retrieval of embolitic material from the lungs pores may be above 250 microns in diameter.

In an exemplary embodiment, porous membrane has an internal volume of 0.3 cubic centimeters or greater, for example within the area defined between porous filter 190 and wall 402, allowing filter 900 to trap significant amounts of particulate debris. Alternatively or additionally, porous membrane has an internal volume of 0.3 cubic centimeters or less, for example, when used in blood vessels of smaller size, and/or in procedures where less debris is generated.

Figure 10C:
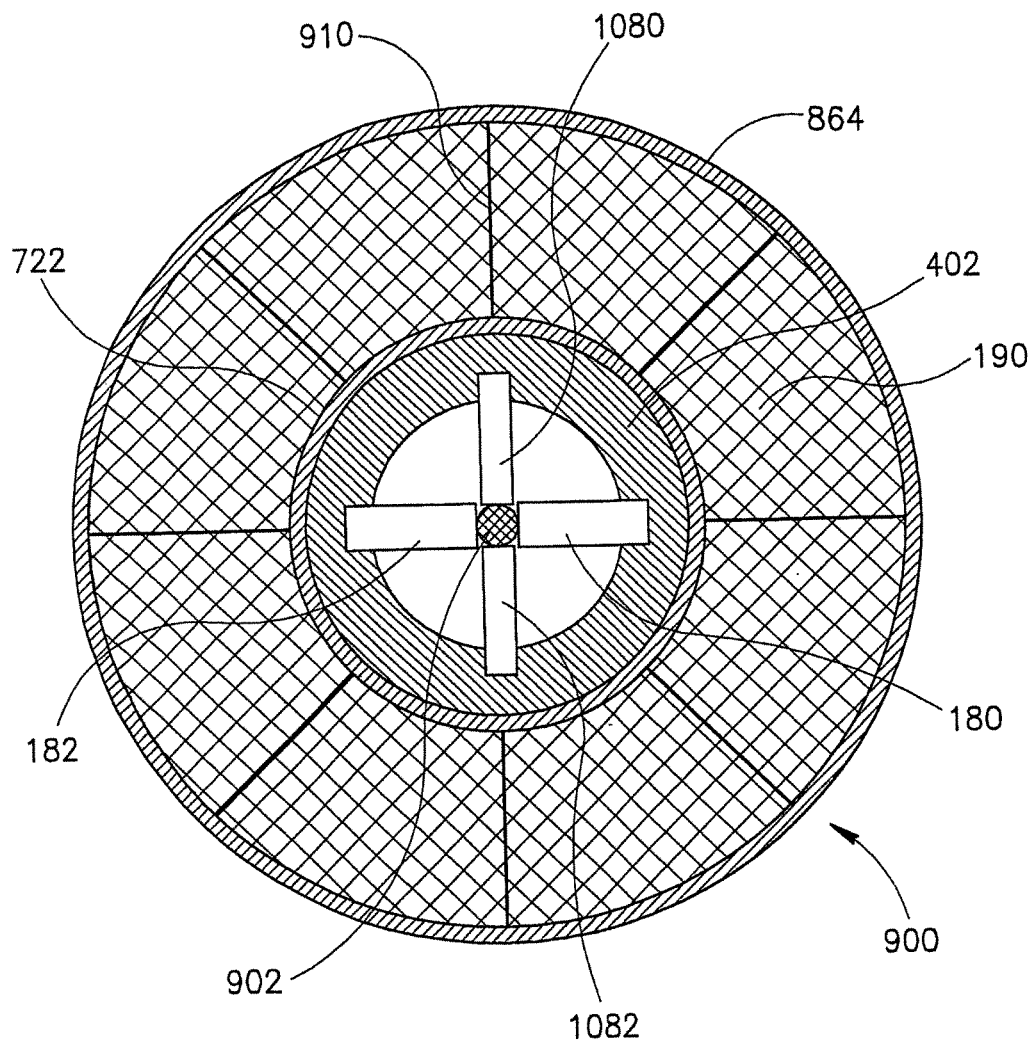
FIG. 10C is a head on view of the filter of FIG. 10A, in accordance with an exemplary embodiment of the invention.

FIG. 10C is a detailed head on view of 900 filter of FIG. 10A, in accordance with an exemplary embodiment of the invention, showing stops 1080 and 1082 in addition to stops 180 and 182 so that guidewire 902 is surrounded by stops 180, 182, 1080 and 1082.

Figure 11:
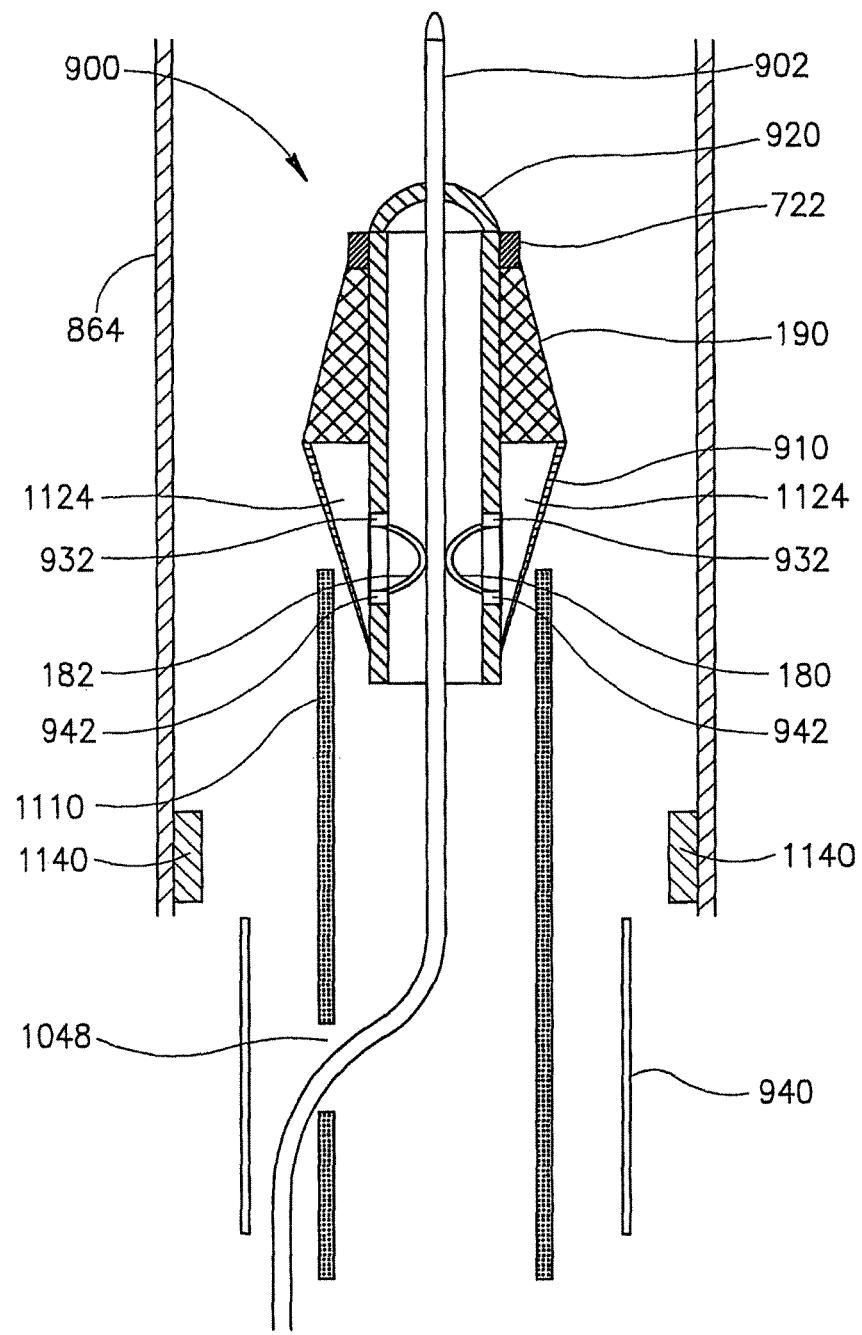
FIG. 11 is a detailed cross sectional view of a filter during removal from a blood vessel, in accordance with an exemplary embodiment of the invention.

FIG. 11 is a detailed cross sectional view of filter 900 during removal from blood vessel 846 following deployment of a stent 1140, in accordance with an exemplary embodiment of the invention.

Removal sheath 1110 is placed on guidewire 902, for example through opening 1048, and moved along guidewire 902, through guide catheter 940 until its front boundary contacts strut 910. As sheath 1110 contacts strut 910, strut 910 moves radially toward guidewire 902 while circumferential ring 722 moves toward and/or past curved tip 920.

In an exemplary embodiment, space 1124 maintains a volume suitable for transporting the particulate and/or gaseous debris during removal of filter 900 from blood vessel. With filter 900 collapsed and partially or totally contained within sheath 150, filter 900 and/or sheath 150, and/or guidewire 902 are pulled through stent 1140, and out of blood vessel 846. Filter 900 is optionally designed to resist deformity during removal so that it fully removes any particulate it captured during its deployment in vessel 864.

An Exemplary Surgical Procedure

In an exemplary embodiment, filter 900 is deployed in and removed from a blood vessel in the following manner:

1. An entry portal is made into an accessible blood vessel 846, for example the femoral artery.
2. A guide catheter and/or dedicated sheath 940 is fed from the femoral artery to the target area
3. Guide wire 902 is fed through guide catheter 940 into blood vessel 864 past, for example, an artheromatous plaque 916 (FIG. 9).
4. Sheath 150, containing filter 900 in the collapsed state, is threaded onto guidewire 902 and moved along blood vessel 864 using sheath 150 to push it forward.
5. Upon reaching or passing the target site, restrainer 132 is removed so that stops 180 and/or 182 deploy to lock filter 900 on guide wire 902.
6. Sheath 150 is removed from filter 900 and filter 900 expands so that membrane 190 spans all or part of the cross sectional diameter of blood vessel 864 and sheath 150 is pulled out of vessel 846, as seen in FIG. 10A.
7. When filter 900 is used in conjunction with a stenting procedure, for example, guide catheter and/or dedicated sheath 940 is fed over guidewire 902 until it reaches the target area and stent 1140 is deployed and anchored in blood vessel 864 while embolitic material is caught by open filter 900 as seen in FIG. 10C, for example downstream of stent 1140.
8. As seen in FIG. 11, following completion of the procedure, removal sheath 1110 is optionally fed onto guidewire 902 and pushed forward in blood vessel 846 until its front boundary contacts struts 910.
9. Sheath 1110 is pressed against struts 910 to cause them to collapse radially and sheath 1110 along with filter 900 and guide wire 902 are removed from blood vessel 864.

Exemplary Specifications

Referring to FIG. 9, rapid exchange guidewire 902 used in a rapid exchange technique, for example, may be flexible anywhere along its length, for example at a flexed section 952 as filter 900 moves along guidewire 902.

To secure filter 100 in place, stops 180 and 182 are designed to each deliver, for example, 100 to 500 grams of force against guide wire 102. However, stops 180 and 182 may be designed to deliver a force less than 100 grams for used in special situations, for example where the displacement force is extremely low, for example in peripheral veins. Alternatively or additionally, stops 180 and 182 may be designed to deliver a force greater than 500 grams, for example, in patients with high blood flow speed, where released emboli are likely to have large mass and/or when a more slippery guide wire is anticipated. Alternatively or additionally, a force greater than 500 grams may be required when guidewire 102 comprises smooth materials that do not provide a friction finish to which stops 180 and 182 secure under lower pressure.

Stops 180 and 182, for example, may be manufactured from resilient material such as surgical grade spring steel. For example, the whole wall 184 including the stops may be cut (e.g., using a laser or other means known in the at) from a sheet of steel or other biocompatible metal, such as titanium, or a nickel titanium alloys. Depending on the implementation, it may be desirable that the filter, body and/or stops be formed of plastic, elastic and/or super elastic materials.

Stops 480 and 482 (FIG. 4), 580 and 582 (FIG. 5), and 680 and 682 (FIG. 6), may be, for example, manufactured from surgical grade polyethylene, nylon and/or terephthalate and/or other flexible, surgical-grade materials suitable for use in the vasculature.

Two stops, 180 and 182 are shown, but filter 100 may comprise less or more stops, for example, depending upon the diameter of guidewire 102, the material from which guidewire 102 is manufactured and/or the design of filter 100.

In an exemplary embodiment, stops 180 and 182 are radially disposed around wire 102, for example so they apply equivalent radial pressure, that will not cause deformation to filter 100. Applying even pressure allows stops 180 and 182 to be positioned between boundaries 122 and 124 (FIGS. 1-3) without distorting the architecture of filter 100 and/or wall 184. Optionally, two or more axially displaced stops (relative to the guidewire) or sets of stops may be used.

In an exemplary embodiment of the present invention, sleeve stop 400 (FIGS. 4-6) is used in conjunction with any number of devices that are delivered into the vasculature. Such devices, for example, may include ablation lasers and/or catheter balloons that are used to ablate intravascular plaques, stents for restoring and/or maintaining patency of blood vessels.

Alternatively or additionally, such devices may include a variety of instrumentation including an arthroscopic tip, laparoscopic tools, and/or artheromatous shavers that are often used in vascular procedures.

While the invention has been described with respect to a limited number of embodiments, it will be appreciated that many variations, modifications and other applications of the invention may be made. In particular, features from one embodiment may be combined with features of another embodiment, in accordance with some embodiments of the present invention.

A variety of values have been utilized to describe the invention including, diameters, lengths and types of materials for the various filters, sleeves and/or stops. Although a variety of values and/or materials have been provided, it should be understood that these could vary even further based upon a variety of engineering principles, materials, intended use and designs incorporated into the invention.

It should be appreciated that different features may be combined in different ways. In particular, stop sleeve may be utilized with other instruments and/or devices used in the vasculature and may be modified in shape, size and/or materials to be ergonomically and engineeringly compatible with the specific usage.

Hence, not all the features, shapes and/or dimensions shown above in a particular embodiment may be necessary in every similar exemplary embodiment of the invention. The particular geometric forms and measurements used to illustrate the invention should not be considered limiting the invention in its broadest aspect to only those forms. Although some limitations are described only as method or apparatus limitations, the scope of the invention also includes apparatus designed to carry out the methods of using the apparatus.

Also within the scope of the invention are surgical kits, for example, kits that include sets of delivery systems, guidewires, filters and/or self-deploying stops. Optionally, such kits also include instructions for use. Measurements are provided to serve only as exemplary measurements for particular cases, the exact measurements applied will vary depending on the application. When used in the disclosure and/or claims, the terms "comprises", "comprising", "includes", "including" or the like mean "including but not limited to".

A person skilled in the art will appreciate that the present invention is not limited by what has thus far been described. Rather, the scope of the present invention is limited only by the following claims.

We claim:

1. A vascular therapeutic device disposed on a guidewire, said therapeutic device having a guidewire stop adapted to selectively stop the therapeutic device from longitudinally moving relative to a guidewire, the therapeutic device comprising:
   a sleeve slideably disposed about the guidewire;
   a vascular therapeutic device secured to the sleeve;
   the actuatable guidewire stop secured within an interior space of the sleeve and comprising one or more radially expandable balloons; and
   an inflation hose connected to the one or more radially expandable balloons for transfer of a fluid into the balloon or balloons,
   wherein the transfer of fluid urges the one or more radially expandable balloons into direct contact with the guidewire to prevent longitudinal movement of the sleeve and the vascular therapeutic device along the guidewire.

2. The guidewire stop of claim 1, wherein the fluid is biologically inert.

3. The guidewire stop of claim 1, wherein the inflation hose is connected to the one or more radially expandable balloons at one or more hose attachment ports which self-seal upon disconnection of the inflation hose from the one or more hose attachment ports.

4. The guidewire stop of claim 3, further comprising a sheath having a leading edge with one or more sharp projections, with the sheath advancing inside the sleeve toward the balloon or balloons, wherein the balloon or balloons deflate upon puncture by the one or more sharp projections.

5. The guidewire stop of claim 1, wherein the inflation hose is connected to the one or more radially expandable balloons at one or more hose attachment ports and the balloon or balloons deflate upon disconnection of the inflation hose from the one or more hose attachment ports.

6. The guidewire stop of claim 1, wherein the vascular therapeutic device is an ablation laser.

7. The guidewire stop of claim 1, wherein the vascular therapeutic device is a catheter balloon.

8. The guidewire stop of claim 1, wherein the vascular therapeutic device is a stent.

9. The guidewire stop of claim 1, wherein the vascular therapeutic device is a atherectomy device.

10. The guidewire stop of claim 9, wherein the atherectomy device is an artheromatous shaver.

11. A method for selectively fixating a vascular therapeutic device at a desired location along a longitudinal position of a guidewire, the vascular therapeutic device being coupled with an actuatable guidewire stop having one or more radially expandable balloons, the method comprising the steps of:
   advancing the vascular therapeutic device, including the actuatable guidewire stop, along the guidewire; and
   inflating the one or more balloons to urge the one or more radially expandable balloons into direct contact with the guidewire to prevent longitudinal movement of the vascular therapeutic device along the guidewire.

12. The method of claim 11, wherein the one or more radially expandable balloons are surrounded by a sleeve.

13. The method of claim 11, wherein the one or more radially expandable balloons are inflated by transfer of a fluid.

14. The method of claim 11, further comprising the step of detaching the guidewire stop from the guidewire by deflating the one or more balloons.

* * * * *